United States Patent [19]
Tran

[11] Patent Number: 5,809,199
[45] Date of Patent: Sep. 15, 1998

[54] BIOCOMPATIBLE OPTICAL FIBER TIP FOR IN VIVO LASER SURGERY

[75] Inventor: Danh Tran, Bethesda, Md.

[73] Assignee: Infrared Fiber Systems, Inc., Silver Spring, Md.

[21] Appl. No.: 717,099

[22] Filed: Sep. 20, 1996

Related U.S. Application Data

[60] Provisional application No. 60/004,099 Sep. 21, 1995.
[51] Int. Cl.$^6$ .................................................. G02B 6/00
[52] U.S. Cl. ............................................................ 385/141
[58] Field of Search .................................. 250/368; 65/425; 123/494, 435, 527; 427/163.2, 512, 513, 517, 487.1; 606/10, 12, 17; 607/89; 385/140, 141, 142, 145

[56] References Cited

U.S. PATENT DOCUMENTS

| | | | |
|---|---|---|---|
| 4,194,807 | 3/1980 | Gliemeroth | 385/141 |
| 4,610,708 | 9/1986 | Sarhangi et al. | 65/3.12 |
| 4,659,355 | 4/1987 | Maze et al. | 65/3.12 |
| 4,778,249 | 10/1988 | Worrell | 385/141 |
| 4,790,619 | 12/1988 | Lines et al. | 385/141 |
| 4,969,941 | 11/1990 | Kyoto et al. | 65/18.1 |
| 4,975,102 | 12/1990 | Edahiro et al. | 65/3.12 |
| 5,024,597 | 6/1991 | Minns et al. | 385/145 |
| 5,093,288 | 3/1992 | Aitken et al. | 501/42 |
| 5,148,510 | 9/1992 | Borrelli et al. | 385/142 |
| 5,168,079 | 12/1992 | Aitken et al. | 501/41 |
| 5,234,835 | 8/1993 | Nestor et al. | 128/633 |
| 5,274,728 | 12/1993 | Tran | 385/142 |
| 5,305,414 | 4/1994 | Higby et al. | 385/142 |
| 5,387,211 | 2/1995 | Saadatmanesh et al. | 606/10 |
| 5,394,852 | 3/1995 | McAkister | 123/494 |
| 5,435,405 | 7/1995 | Schempf | 901/1 |
| 5,484,822 | 1/1996 | Minns | 522/35 |
| 5,491,767 | 2/1996 | McPherson et al. | 385/123 |
| 5,492,987 | 2/1996 | Minns | 526/245 |
| 5,534,558 | 7/1996 | Minns | 427/163.2 |
| 5,580,086 | 12/1996 | McAlister | 280/737 |
| 5,640,017 | 6/1997 | Thevenin | 250/368 |

*Primary Examiner*—Akm E. Ullah
*Attorney, Agent, or Firm*—Browdy and Neimark

[57] ABSTRACT

A biocompatible optical fiber tip derived from fluorophosphate glasses whose composition includes P—O compounds, AlF$_3$, alkali-earth fluorides, and/or alkali fluorides, and lanthanides fluoride is used with a medical laser to transmit power for surgical applications.

16 Claims, 3 Drawing Sheets

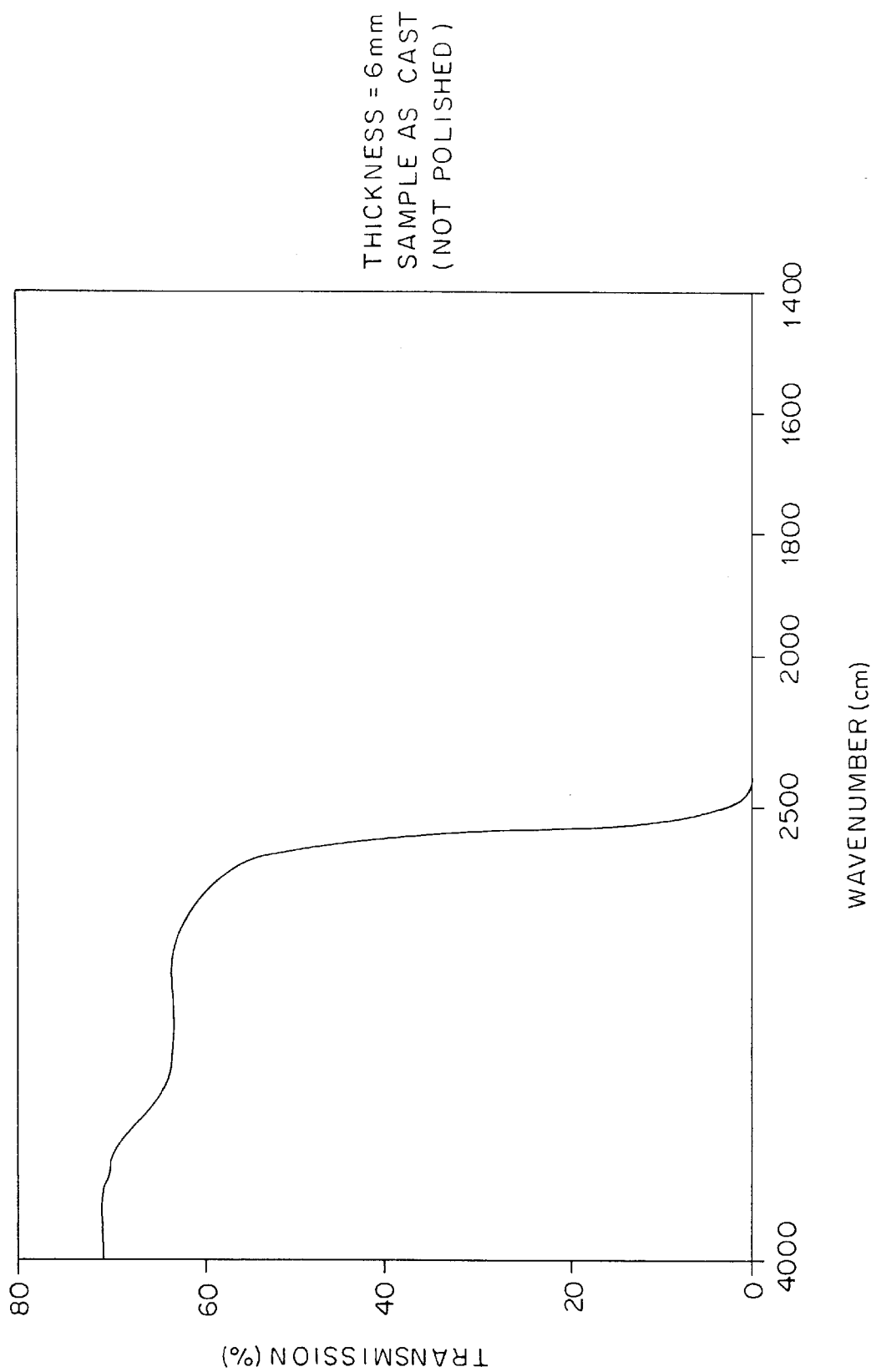

BIOCOMPATIBLE OPTICAL FIBER TIP FOR IN VIVO LASER SURGERY

This application claims benefit under 35 U.S.C. 119(e) of parent co-pending provisional application Ser. No. 60/004,099, entitled "Biocompatible Optical Fiber for Laser Surgery", filed Sep. 21, 1995.

FIELD OF INVENTION

The present invention relates to laser surgery, and more particularly to an optical fiber for use in in vivo laser surgery for transmitting laser power radiation, particularly at the mid-IR range about from 1–4 µm, comprising a trunk fiber and an improved biocompatible tip.

BACKGROUND

The use of lasers in medical surgery has been growing at a fast pace. Lasers are used for varied applications such as the ablation of hard and soft tissues in both general and dental surgery. Fiber optics plays an important role in most laser surgical procedures. The laser energy can be elegantly delivered to the tissue area via an optical fiber, about 200 cm long, thus avoiding the use of bulky traditional reflective optics. Up to now quartz and sapphire fibers have been used as fiber delivery system for in vivo surgery since both materials are biocompatible and will not be harmful to the human body.

There are, however, several disadvantages in both quartz fibers and sapphire fibers including brittleness, poor optical transmissibility, etc., as will be elaborated upon below. As a result, it has been more customary to use combination optical fibers including a trunk fiber of about 200 cm consisting of a non-biocompatible fiber which is butt-coupled to a much shorter quartz or sapphire tip of about 2.5–12 cm which will interact with the tissue.

Even for these shorter lengths, however, there are several disadvantages in both quartz fibers and sapphire fibers. Quartz fibers transmit very poorly above 2.5 µm and thus exhibit high optical loss when used with Mid-Infrared (Mid-IR) lasers such as the Er:YAG which operates at 2.94 µm. For example, only 30 percent of the Er:YAG laser power can be transmitted over a 12 cm quartz fiber tip. Sapphire fibers transmit better but because sapphire is a crystalline material, the fibers experience the following drawbacks:

(1) Sapphire fibers are very rigid and often rupture upon bending.
(2) Mechanical cleaving cannot be used for fiber end preparation. Mechanical polishing, which is much more labor intensive and thus expensive, is required.
(3) In many surgical procedures, it is often required to shape the tip of the fiber to optimize the focusing of the laser beam. For example, tapered tips, tips terminated with a spherical lens or bent tips are commonly used. Tip shaping can be readily achieved by just re-heating and re-forming the tip of a glass fiber, but this re-heating process cannot be applied to a crystalline material such as a sapphire tip.
(4) Crystal grown sapphire fibers are much more expensive than glass fibers because the growth process is much slower than the glass fiber drawing process.

Fluorophosphate (FP) glasses, i.e. glasses which contain metal fluorides and P—O compounds in the form of $P_2O_5$, $Al(PO_3)_3$, $Ba(PO_3)_2$, $Mg(PO_3)_2$ or $NaPO_3$, have been known for many years (J. T. Wetzel et al, "Development of Fluorophosphate Optical Glasses", SPIE Vol. 204, Physical Properties of Optical Materials, 1979). Because of their relatively low refractive index and low optical dispersion, these glasses have been investigated for use as high power laser windows mostly in military applications. Thus, a laser beam when passing through an FP glass window will experience minimal reflection because of the low index and minimal deflection because of the low dispersion of the glass.

A typical FP glass system consists of a P—O compound which is the primary glass former, $AlF_3$ as the secondary glass former, $RF_2$ and/or MF, and $LnF_3$ as glass modifiers, where R=alkaline-earth metal (Ca, Mg, Ba, . . . ) and M=alkali metal (Na, Li. K, . . . ), and Ln=lanthanide (La, Y, Sc . . . ). The chemical durability, the glass forming ability and the optical transmission of the FP glass depend very much on the nature as well as the concentration of the glass components. For example FP glasses which contain large amounts of $P_2O_5$, $NaPO_3$, $KPO_3$, LiF or NaF are relatively soluble in water; FP glasses which contains small amounts of P—O have high tendency for crystallization; FP glasses which contains large amounts of P—O exhibit high stability but transmit very poorly in the Mid-IR spectral region due to the broad P—O absorption band centered at at 4.5 µm. In addition, water of dehydration which is associated with P—O compounds absorbs strongly around 2.9 µm, thus suggesting FP glasses would not be good candidates for in vivo optical laser fibers for use in the mid-IR range.

The Tran U.S. Pat. No. 5,274,728 discloses heavy metal-oxide glass optical fibers for use in laser medical surgery, including phosphate and fluorophosphate glasses. See for example column 5, lines 47–63, and Example 6. However, this patent provides no disclosure or suggestion that fluorophosphate glasses are highly biocompatible, and therefore would serve well in place of quartz or sapphire tips for in vivo surgery.

SUMMARY OF INVENTION

It is accordingly an object of the present invention to overcome deficiencies in the prior art, such as indicated above.

It is another object to provide butt-coupled trunk-tip optical fibers for in vivo surgery wherein the tip is formed of an FP glass of low water solubility.

It is a further object to provide such a biocompatible fiber which exhibits high optical transmission ranging from the UV to the mid-IR spectral region.

Yet a further object is to provide a novel FP tip for a butt-coupled optical fiber for in vivo surgery having high chemical durability, excellent biocompatibility, high optical transmission in the mid IR range, and high stability such that the FP glasses can be drawn into optical fiber for ready and inexpensive manufacture into tips.

These objectives are generally accomplished by the use of FP glasses, including those disclosed in the aforementioned Tran U.S. patent '728, having quantities of P—O compounds of less than 25 mol % and preferably less than 12 mol %, and quantities of MF compounds less than 15%.

BRIEF DESCRIPTION OF DRAWING

Further objects and the nature and advantages of the present invention will be more apparent from the following detailed description of embodiments taken in conjunction with the drawing, wherein:

FIG. 4 is a graph of a spectral curve of a conventional and less suitable glass for use in accordance with the present invention, containing 18 mol % $Al(PO_3)_3$.

DETAILED DESCRIPTION OF EMBODIMENTS

Figure 1:
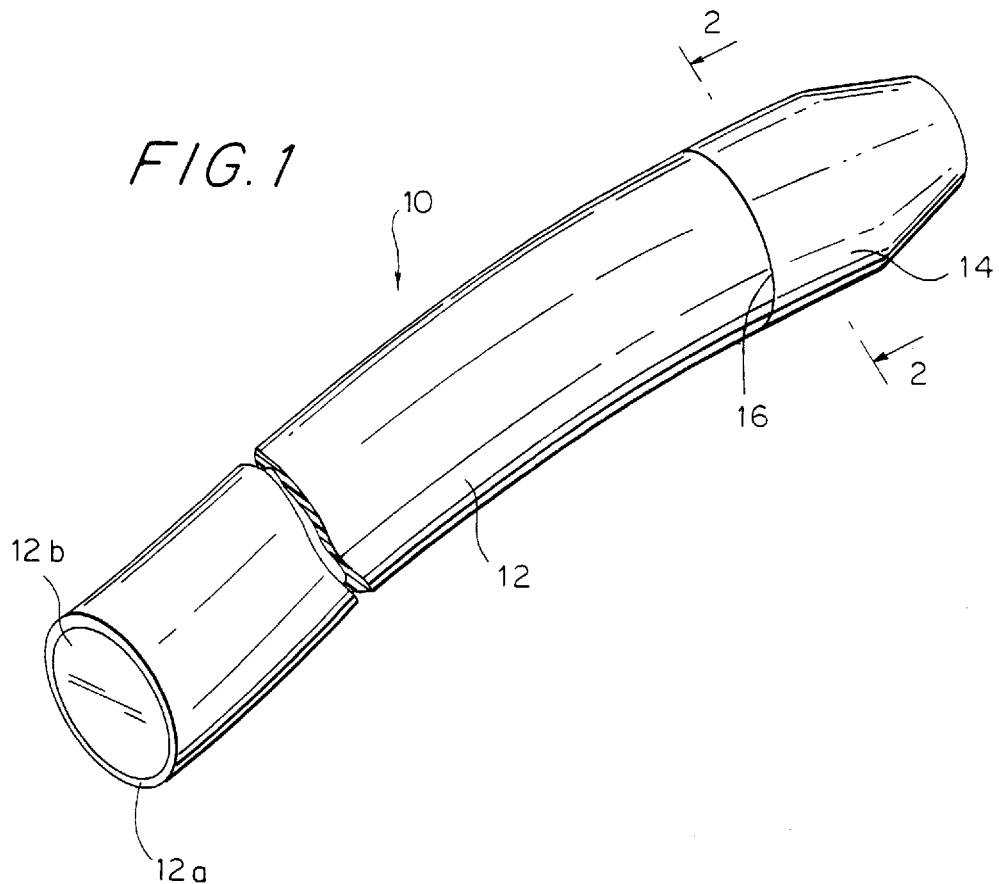
FIG. 1 is a schematic perspective view of an optical fiber according to the present invention, suitable for laser surgery.

FIG. 1 shows a composite optical fiber 10 in accordance with the present invention comprising a suitable optical trunk fiber 12, such as a germanium oxide fiber in accordance with Tran U.S. patent '728, and a special biocompatible tip 14 in accordance with the present invention. The trunk fiber 12 comprises a glass cladding 12a and a core 12b, both as disclosed in Tran U.S. patent '728, and may be overcoated with a thin plastic sheath (not shown). The proximal end of the tip 14 and the distal end of the fiber 12 are each preferably mechanically cleaved or optionally polished, and butt-coupled along their contacting plane surfaces as shown at 16.

Figure 2:
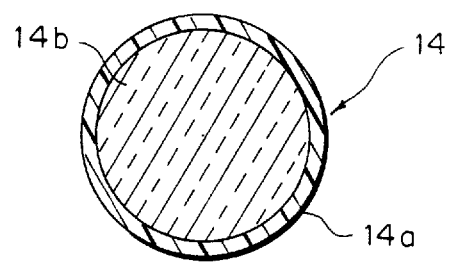
FIG. 2 is a sectional view taken along line 2—2 of FIG. 1.

The tip 14 can take a variety of shapes, and in the illustrated embodiment is shown as having a cylindrical proximal portion and a frusto-conical distal portion; however, it will be understood that many other shapes are possible including tapered tips, tips terminated with a spherical lens or bent tips. The glass core of the tip 14 is shown at 14b in FIG. 2. While both ends of the core 14b are uncoated, the sidewall of the FP glass core 14b of the tip 14 is provided with a polymeric coating or cladding 14a, which coating 14a must be non-toxic and otherwise biocompatible, and which may be selected from among the fluoropolymers usually used for this purpose in conjunction with quartz and sapphire tips, including TEFLON FEP (Teflon™).

Figure 3:
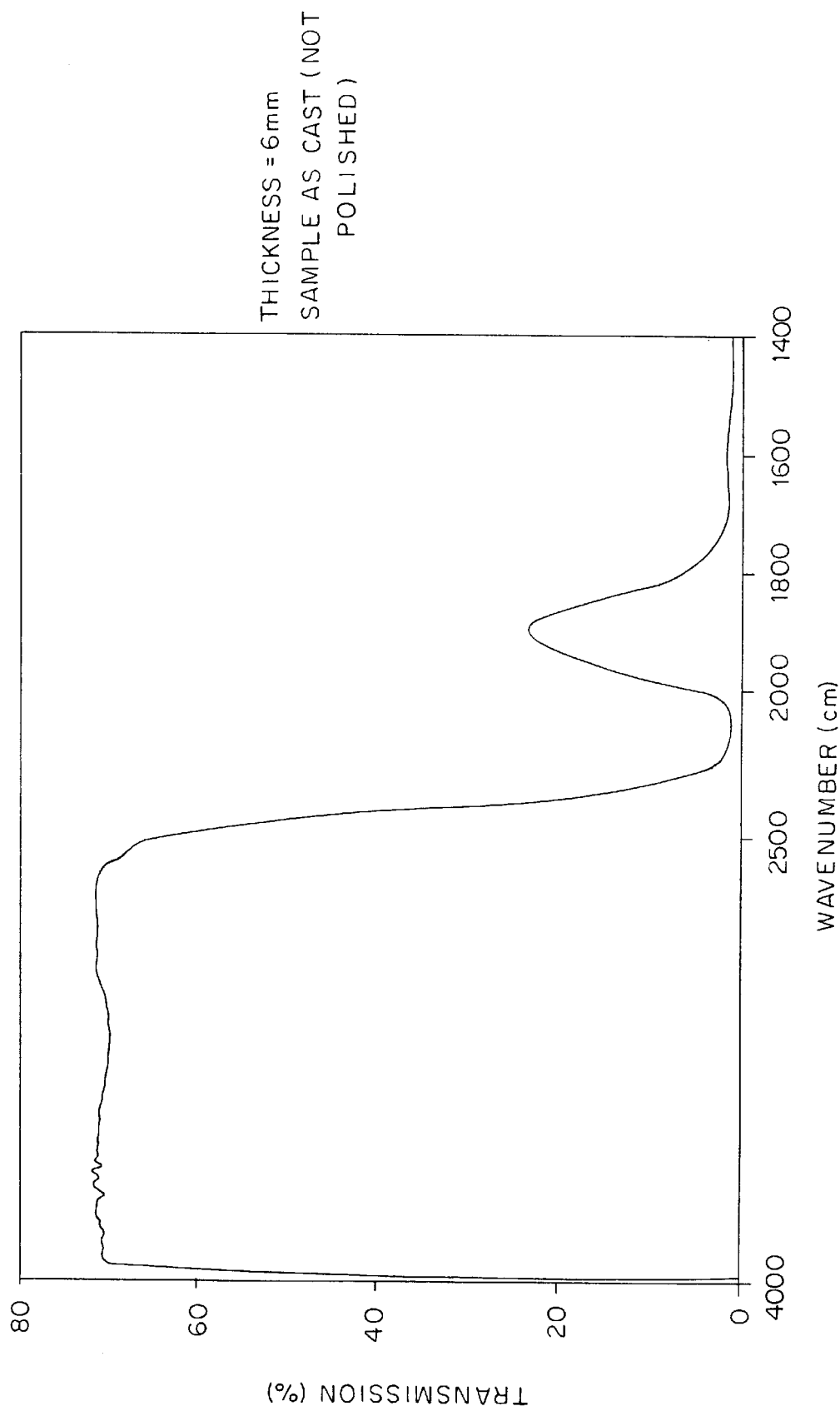
FIG. 3 is a graph of a spectral curve of a fluorophosphate glass suitable for use in accordance with the present invention, containing 6 mol % of $Al(PO_3)_3$.

A key feature of the present invention is the proper selection of the glass 14b used for the in vivo tip 14. These FP glasses mainly consist of P—O compounds in the form of $P_2O_5$, $Al_2(PO_3)_3$, $Ba(PO_3)_2$, $Mg(PO_3)_2$ and/or $NaPO_3$ in a total amount of no more than 25 mol % (but preferably at least 1.5 mol %) 20–45 mol % $AlF_3$, 25–65 mol % $RF_2$ where R=alkaline-earth metal (Ca, Mg, Ba, . . . ), no more than 25 mol % $LnF_3$ where Ln=lanthanide (La, Y, Sc, . . . ) and no more than 15 mol % MF where M=alkali metal (Na, Li, K, . . . ). Preferably, however, the glass 14b of the tip 14 of the laser fiber of the present invention contains no more than 12 mol % of P—O compounds. These parameters are necessary in order to ensure high chemical durability and low solubility in water so that the tip is fully biocompatible and can be safely used in vivo in medical laser surgery, and also to provide superior transmission of light in the mid-IR range. The spectral curves of a new FP glass containing 6 mol % $Al(PO_3)_3$ of composition $6Al(PO_3)_3$-$31.5AlF_3$-$12NaF$-$8MgF_2$-$26.5CaF_2$-$8SrF_2$-$8BaF_2$, and a conventional FP laser window glass containing 18 mol % $Al(PO_3)_3$ of composition 18 Al ($PO_3$-$10AlF_3$-$22NaF$-$8.5MgF_2$$25CaF_2$- $8SrF_2$-$8.5BaF_2$, shown respectively in FIG. 3 and FIG. 4, indicate a much higher transmission obtained for the new glass of FIG. 3.

The new FP glasses also exhibit high resistance to water attack and are biocompatible as shown by cytotoxicity elution testing. These FP glasses are stable enough to be drawn into optical fibers without crystallization. When tested with an Er:YAG laser at 2.94 μm, FP fibers 500 μm in diameter and about 12 cm long exhibit about 80% transmission which is comparable to sapphire fibers and almost three times better than quartz fibers. These FP fibers can handle more than 10 Watts of Er:YAG laser power. This high power level is more than sufficient for most surgical procedures including the hardest tissue, such as tooth enamel.

In more detail, it has now been discovered that the aforementioned requirements of high chemical durability, low water solubility, and superior biocompatibility and transmission in the mid-IR range dictate that the glass must contain limited amounts of both phosphates and alkyl fluorides. Phosphates, such as $Al(PO_3)_3$, $P_2O_5$, $Ba(PO_3)_2$, $Mg(PO_3)_2$ and $NaPO_3$, must be limited in quantity in order to have better transmission in the Mid-IR; and the amounts of soluble components such as $P_2O_5$ or alkali fluorides, namely NaF and LiF, must be limited for biocompability purposes. Suitable compositions of typical fluorophosphate glass of the present invention are given in Tables 1 and 2.

The fluorophosphate glasses of the examples given above and in the Tables 1 and 2 were prepared using 99.9999% high purity starting chemicals. Each glass batch weighing 30 g was melted in platinum crucible inside a dry box under an Argon atmosphere containing less than 1 ppm water. The melting schedule was set at 950° C. for one hour and the refining step was carried out at 850° C. for one hour. The melt was cast into a brass mold heat-treated at 410° C. and slowly cooled down to room temperature.

TABLE 1

Typical Fluorophosphate glasses of the invention.
COMPOSITION

| Glass # | $Al(PO_3)_3$ | $P_2O_5$ | $Ba(PO_3)_2$ | $Mg(PO_3)_2$ | $NaPO_3$ | $Al_2O_3$ | $AlF_3$ | $RF_2$ | MF | LnF |
|---|---|---|---|---|---|---|---|---|---|---|
| MP12 | 4 | | | | | | 32 | 56 | 8 | |
| MP14 | 5 | | | | | | 32 | 51 | 12 | |
| MP20C | | 4.6 | | | | 1 | 33 | 43 | | 1 |
| MP20D | 0.9 | 4 | | | | 0.3 | 29.6 | 51.4 | | 13.8 |
| MP23 | 6.9 | | | | | 2 | 18.7 | 58.5 | 13.4 | |
| MP29 | | | 8 | | | | 40 | 41 | 10 | |
| MP30 | | | | | 13 | | 25.5 | 61.5 | | |
| MP31 | | | | 10 | | | 26 | 64 | | |

TABLE 2

Values of R, M and Ln for typical fluorophosphate glasses of the invention
FLUORIDE COMPOUNDS (MOL %)

| | R Values | | | | M Values | | Ln Values |
|---|---|---|---|---|---|---|---|
| Glass # | $MgF_2$ | $CaF_2$ | $SrF_2$ | $BaF_2$ | LiF | NaF | $YF_3$ |
| MP12 | 9 | 29 | 9 | 9 | | | |
| MP14 | 8 | 27 | 8 | 8 | | 12 | |
| MP20C | 8 | 20 | 8 | 7.4 | | | 18 |
| MP20D | 9.4 | 23 | 10 | 9 | | | 13.8 |
| MP23 | 7 | 16.4 | 23.6 | 12 | 12.4 | 1 | |
| MP29 | 10 | 16 | 10 | 5 | | 10 | |

TABLE 2-continued

Values of R, M and Ln for typical fluorophosphate glasses of the invention
FLUORIDE COMPOUNDS (MOL %)

| Glass # | R Values | | | | M Values | | Ln Values |
|---|---|---|---|---|---|---|---|
| | $MgF_2$ | $CaF_2$ | $SrF_2$ | $BaF_2$ | LiF | NaF | $YF_3$ |
| MP30 | 20.5 | 20.5 | | 20.5 | | | |
| MP31 | 13 | 23 | 14 | 14 | | | |

Two standard methods were employed to measure the water resistance of the glass:

(1) In the Powdered Glass test method, each of the fluorophosphate glasses investigated was ground and sieved to collect particle size of 420–590 μm. The powdered glass was weighed and placed in a platinum net basket and soaked in 80 ml de-ionized water contained in a silica beaker. The glass was boiled for 60 minute. The percentage of weight loss was then measured. All the glasses of Table 1 showed a weight loss of less than 0.04. This low weight loss level is classified under Class 1, the highest water-durability classification obtained in glass (HOYA Optical Class Technical Data—HOYA Corp., Tokyo, Japan).

(2) In the Intrinsic Chemical Durability to Water test, the conditions were similar to the Powdered Glass test, except that the FP glass solubility was evaluated in terms of weight loss per unit area $[10^{-3}$ mg/(cm$^2$·hr)$]$ for a given period of time. All glasses studied exhibited a weight loss of less than 0.3 $[10^{-3}$ mg/(cm$^2$·hr)$]$ which is also classified under Class 1 (HOYA Optical Glass Technical Data). This result reflected the biocompatible nature of the MP2OC glass as shown by the above-mentioned cytotoxicity elution test.

Fluorophosphate fibers, 500 μm in diameter were drawn from each of the glass compositions studied. The fibers were coated with TEFLON FEP which acted as the optical cladding material. The cladding thickness was around 20 μm. Each fiber were cut to the desired size and was tested in terms of its power handling as well as its optical throughput using an Mid-IR laser, namely an Er:YAG laser operating at 2.94 μm. Prior to the test measurements, the ends of each fiber were carefully cleaved using a cleaving knife equipped with a diamond blade. The laser radiation, $I_i$, was focused on the input end of the fiber via a $CaF_2$ lens having a 22 mm focal length. The output power, $I_o$, was obtained using a radiometer set to measure ten consecutive pulses. The resulting values of $I_i$, $I_o$, the fiber length under test, the power coupling efficiency and the condition of each fiber after test are shown in Table 3.

Fibers with higher phosphate concentration, i.e. from 12–25 mol % P—O, can also be used in surgical applications where short fiber tips are applicable, so long as the $P_2O_5$ concentration is kept low.

Fibers with low phosphate content exhibited transmission near 80 percent while lower power throughput was obtained with the high phosphate content fibers. Also, it can be expected that the loss will be higher at input laser power of 1,000 mJ for the same fiber. This can be attributed to the high divergence of the input laser beam arising from thermal lensing which overfilled the core of the fiber.

TABLE 3

Power handling and transmission characteristics of typical fluorophosphate glasses of the invention using an Er:YAG laser

| Fiber # | Glass Type | Fiber Length (cm) | $I_i$ (mJ) | $I_o$ (mJ) | Coupling Efficiency (%) | Fiber Conditions |
|---|---|---|---|---|---|---|
| 1 | MP12 | 10 | 100 | 81 | 81 | There |
| | | | 1000 | 690 | 69 | was |
| 2 | MP14 | 10 | 100 | 77 | 77 | no damage |
| | | | 1000 | 650 | 65 | after |
| 3 | MP20C | 10 | 100 | 78 | 78 | maximum |
| | | | 1000 | 670 | 67 | duration |
| 4 | MP20D | 10 | 100 | 79 | 79 | of test of |
| | | | 1000 | 650 | 65 | 15 minutes |
| 5 | MP23 | 10 | 100 | 50 | 50 | |
| | | | 1000 | 400 | 40 | |
| 6 | MP29 | 10 | 100 | 41 | 41 | |
| | | | 1000 | 280 | 28 | |
| 7 | MP30 | 10 | 100 | 29 | 29 | |
| | | | 1000 | 190 | 19 | |
| 8 | MP31 | 10 | 100 | 33 | 33 | |
| | | | 1000 | 220 | 22 | |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. The means and materials for carrying out various disclosed functions may take a variety of alternative forms without departing from the invention. It is to be understood that the phraseology or terminology employed herein is for the purpose of description and not of limitation.

What is claimed is:

1. In an in vivo optical fiber for in vivo laser surgery using IR laser light, comprising a trunk fiber and a tip fiber, the improvement wherein said tip fiber is a fluorophosphate glass containing no more than 25 mol % of P—O compounds and no more than 15 mol % of alkali fluorides, said glass having high chemical durability, low solubility in water and superior biocompatibility and power transmission in the mid IR range.

2. An in vivo optical fiber according to claim 1, having a length of about 2.5–12 cm.

3. An in vivo optical fiber according to claim 1, wherein said fluorophosphate glass contains no more than 12 mol % of P—O compounds.

4. An in vivo optical fiber according to claim 1, wherein said fluorophosphate glass contains 20–45 mol % $AlF_3$ and 25–65 mol % of $RF_2$, wherein R is an alkaline earth metal, and optionally no more than 25 mol % $LnF_3$ and optionally no more than 15 mol % MF where M is an alkali metal.

5. An in vivo optical fiber according to claim 1, containing $Al(PO_3)_3$, $P_2O_5$, $Ba(PO_3)_2$, $Mg(PO_3)_2$, $NaPO_3$, or a mixture thereof in a total amount not less than 1.5 mol %.

6. An in vivo optical fiber according to claim 2, wherein said fluorophosphate glass contains no more than 12 mol % of P—O compounds.

7. An in vivo optical fiber according to claim 2, wherein said fluorophosphate glass contains 20–45 mol % $AlF_3$ and 25–65 mol % of $RF_2$, wherein R is an alkaline earth metal, and optionally no more than 25 mol % $LnF_3$ and optionally no more than 15 mol % MF where M is an alkali metal.

8. An in vivo optical fiber according to claim 3, wherein said fluorophosphate glass contains 20–45 mol % $AlF_3$ and 25–65 mol % of $RF_2$, wherein R is an alkaline earth metal, and optionally no more than 25 mol % $LnF_3$ and optionally no more than 15 mol % MF where M is an alkali metal.

9. An in vivo optical fiber according to claim 6, wherein said fluorophosphate glass contains 20–45 mol % $AlF_3$ and 25–65 mol % of $RF_2$, wherein R is an alkaline earth metal, and optionally no more than 25 mol % $LnF_3$ and optionally no more than 15 mol % MF where M is an alkali metal.

10. An in vivo optical fiber according to claim 2, containing $Al(PO_3)_3$, $P_2O_5$, $Ba(PO_3)_2$, $Mg(PO_3)_2$, $NaPO_3$, or a mixture thereof in a total amount not less than 1.5 mol %.

11. An in vivo optical fiber according to claim 3, containing $Al(PO_3)_3$, $P_2O_5$, $Ba(PO_3)_2$, $Mg(PO_3)_2$, $NaPO_3$, or a mixture thereof in a total amount not less than 1.5 mol %.

12. An in vivo optical fiber according to claim 4, containing $Al(PO_3)_3$, $P_2O_5$, $Ba(PO_3)_2$, $Mg(PO_3)_2$, $NaPO_3$, or a mixture thereof in a total amount not less than 1.5 mol %.

13. An in vivo optical fiber according to claim 6, containing $Al(PO_3)_3$, $P_2O_5$, $Ba(PO_3)_2$, $Mg(PO_3)_2$, $NaPO_3$, or a mixture thereof in a total amount not less than 1.5 mol %.

14. An in vivo optical fiber according to claim 7, containing $Al(PO_3)_3$, $P_2O_5$, $Ba(PO_3)_2$, $Mg(PO_3)_2$, $NaPO_3$, or a mixture thereof in a total amount not less than 1.5 mol %.

15. An in vivo optical fiber according to claim 8, containing $Al(PO_3)_3$, $P_2O_5$, $Ba(PO_3)_2$, $Mg(PO_3)_2$, $NaPO_3$, or a mixture thereof in a total amount not less than 1.5 mol %.

16. An in vivo optical fiber according to claim 9, containing $Al(PO_3)_3$, $P_2O_5$, $Ba(PO_3)_2$, $Mg(PO_3)_2$, $NaPO_3$, or a mixture thereof in a total amount not less than 1.5 mol %.

* * * * *